(12) United States Patent
Yaacobi

(10) Patent No.: US 9,687,387 B2
(45) Date of Patent: Jun. 27, 2017

(54) SYSTEM AND METHODS FOR TREATING EAR DISORDERS

(76) Inventor: Yoseph Yaacobi, Fort Worth, TX (US)

( * ) Notice: Subject to any disclaimer, the term of this patent is extended or adjusted under 35 U.S.C. 154(b) by 0 days.

(21) Appl. No.: 14/125,533

(22) PCT Filed: Sep. 14, 2012

(86) PCT No.: PCT/US2012/055408
§ 371 (c)(1),
(2), (4) Date: Dec. 11, 2013

(87) PCT Pub. No.: WO2013/040352
PCT Pub. Date: Mar. 21, 2013

(65) Prior Publication Data
US 2014/0107423 A1    Apr. 17, 2014

Related U.S. Application Data

(60) Provisional application No. 61/534,986, filed on Sep. 15, 2011.

(51) Int. Cl.
| A61F 11/00 | (2006.01) |
| A61M 31/00 | (2006.01) |
| A61B 1/227 | (2006.01) |
| A61K 9/00 | (2006.01) |

(52) U.S. Cl.
CPC ............. *A61F 11/00* (2013.01); *A61B 1/227* (2013.01); *A61K 9/0046* (2013.01); *A61M 31/002* (2013.01); *A61F 2250/0067* (2013.01)

(58) Field of Classification Search
CPC .... A61F 2250/0067; A61F 2250/0068; A61M 3/0279; A61M 31/00; A61M 31/002; A61M 5/14276; A61K 9/0046; A61B 1/227
See application file for complete search history.

(56) References Cited

U.S. PATENT DOCUMENTS

| 3,528,419 | A | * | 9/1970 | Amoroso | A61D 7/00 604/286 |
| 4,034,759 | A | * | 7/1977 | Haerr | 604/514 |
| 4,096,230 | A | * | 6/1978 | Haerr | 264/321 |
| 4,887,999 | A | * | 12/1989 | Alles | 604/110 |
| 5,350,580 | A | * | 9/1994 | Muchow et al. | 424/437 |
| 5,572,594 | A | * | 11/1996 | Devoe | H04R 25/656 181/130 |
| 5,629,008 | A | * | 5/1997 | Lee | A61K 9/0024 424/424 |
| 5,674,196 | A | * | 10/1997 | Donaldson et al. | 604/93.01 |
| 5,744,166 | A |   | 4/1998 | Illum | |

(Continued)

OTHER PUBLICATIONS

Non-Final Office Action dated Jan. 26, 2015 from U.S. Appl. No. 13/417,159.

(Continued)

*Primary Examiner* — Andrew Gilbert
(74) *Attorney, Agent, or Firm* — Teresa J. Schultz

(57) ABSTRACT

An apparatus for insertion in an ear is provided in one example and includes a drug delivery device for insertion into an external auditory canal, wherein the drug delivery device contains one or more pharmaceutically active agents that can be released from the drug delivery device into the external auditory canal. In more particular instances, the drug delivery device can conform to the profile of the external auditory canal.

12 Claims, 7 Drawing Sheets

(56) References Cited

U.S. PATENT DOCUMENTS

| | | | |
|---|---|---|---|
| 5,843,930 A | 12/1998 | Purwar et al. | |
| 5,954,682 A * | 9/1999 | Petrus | A61F 11/00 128/898 |
| 6,152,873 A * | 11/2000 | Rogers | 600/200 |
| 6,238,650 B1 | 5/2001 | Lapidot et al. | |
| 6,358,231 B1 * | 3/2002 | Schindler | A61F 11/00 604/1 |
| 6,521,213 B1 | 2/2003 | Mautone | |
| 6,685,697 B1 * | 2/2004 | Arenberg et al. | 604/890.1 |
| 6,719,750 B2 * | 4/2004 | Varner et al. | 604/289 |
| 6,764,470 B2 * | 7/2004 | Dimick | 604/217 |
| 7,220,431 B2 * | 5/2007 | Sawchuk | A61K 9/0046 400/485 |
| 7,824,699 B2 * | 11/2010 | Ralph | A61K 9/0024 424/422 |
| 8,030,362 B2 * | 10/2011 | Eilat | A61K 9/0046 424/400 |
| 8,568,348 B2 * | 10/2013 | Vlodaver et al. | 604/43 |
| 9,211,374 B2 * | 12/2015 | Wallace | A61M 5/00 |
| 2004/0267241 A1 * | 12/2004 | Russell | A61M 5/14276 604/892.1 |
| 2005/0271706 A1 * | 12/2005 | Anderson et al. | 424/427 |
| 2006/0253087 A1 * | 11/2006 | Vlodaver et al. | 604/275 |
| 2008/0254095 A1 * | 10/2008 | Ma | A61K 9/0024 514/1.1 |
| 2008/0262468 A1 * | 10/2008 | Clifford et al. | 604/501 |
| 2009/0218729 A1 * | 9/2009 | Pelley | 264/297.1 |
| 2009/0299379 A1 * | 12/2009 | Katz et al. | 606/109 |
| 2009/0311304 A1 * | 12/2009 | Borck | A61F 2/86 424/426 |
| 2010/0121285 A1 * | 5/2010 | Illi et al. | 604/286 |

OTHER PUBLICATIONS

Article 34 Amendment dated Apr. 29, 2013 from counterpart PCT App. No. PCT/US2012/055408.

International Preliminary Report on Patentability issued by the IPEA/US in the corresponding PCT application PCT/US12/55408 dated Jul. 29, 2013.

International Search Report issued by the IPEA/US in the corresponding PCT application PCT/US12/55408 dated Nov. 28, 2012.

* cited by examiner

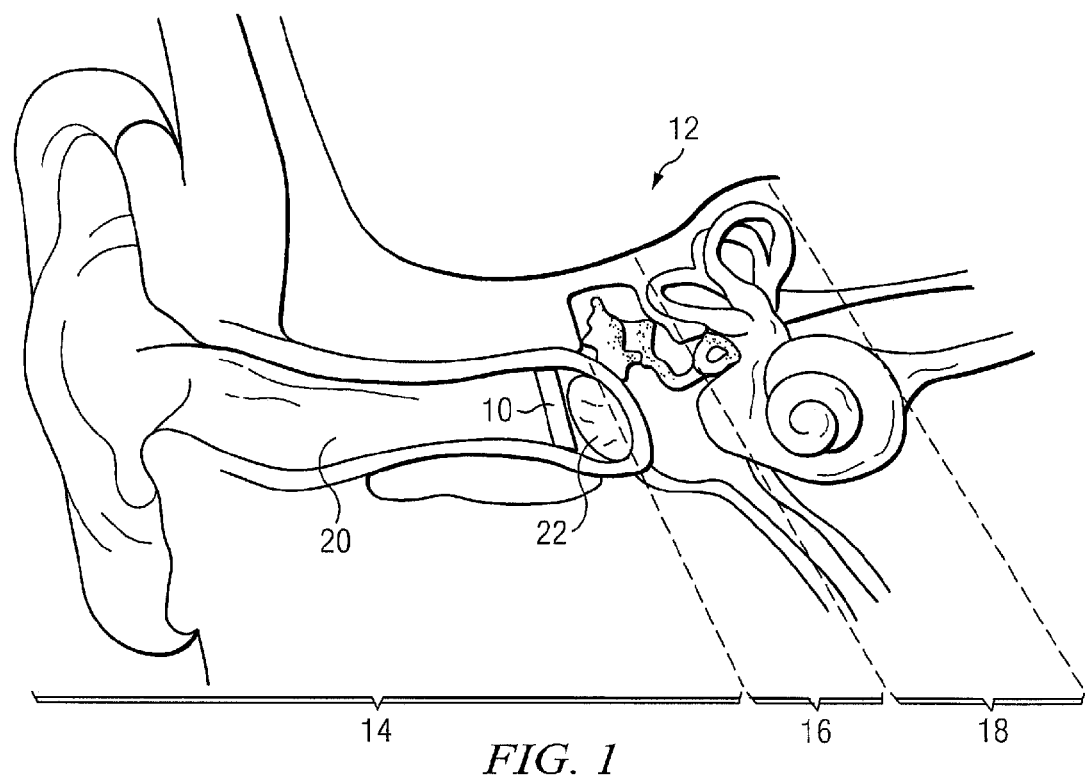
FIG. 1
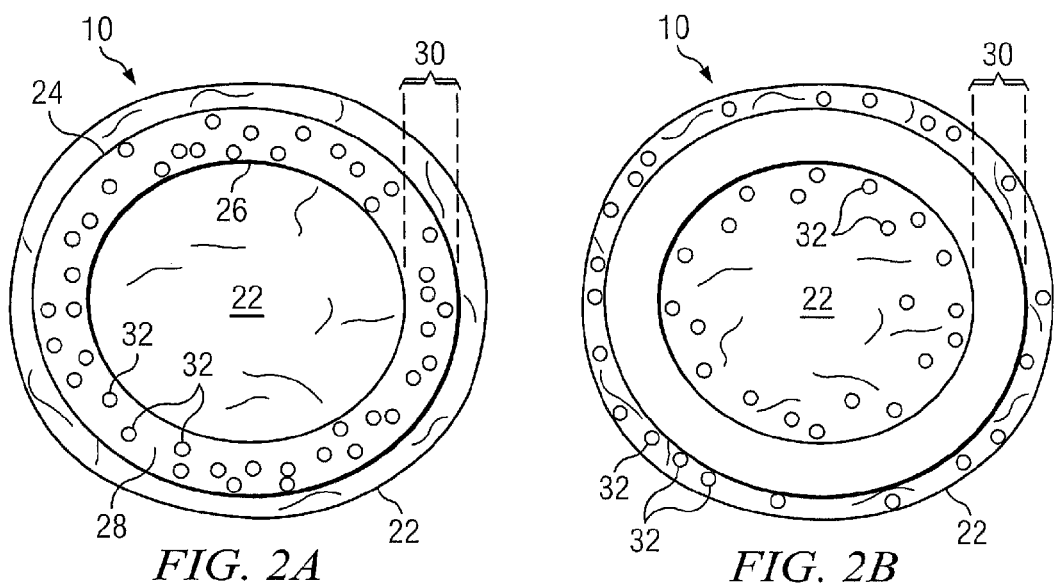
FIG. 2A
FIG. 2B

SYSTEM AND METHODS FOR TREATING EAR DISORDERS

TECHNICAL FIELD

The present disclosure relates in general to the field of pharmaceutics and, more particularly, to treating ear disorders.

BACKGROUND

The ear—the organ responsible for hearing and balance—may be affected by various auricular maladies. One example is infection of the middle ear area, also known as otitis media, which may be manifested as local auricular pain, often associated with systemic symptoms such as fever, nausea, vomiting, and diarrhea. Some patients may also describe unilateral hearing impairment. Diagnosis is based on otoscopy—a visual inspection of the ear and ear-drum, also known as tympanic membrane—which may show a bulging and erythematous tympanic membrane with indistinct landmarks and displacement of the light reflex. Spontaneous perforation of the tympanic membrane may cause sero-sanguineous or purulent discharge from the ear, known as otorrhea. Although acute otitis media may occur at any age, it is most common between ages 3 months and 3 years. At this age range, the eustachian tube—a narrow channel connecting the middle ear with the naso-pharynx—is wider, shorter, and more horizontal than in adults. Etiology of acute otitis media may be bacterial or viral—the latter is often complicated by secondary bacterial infection.

Acute otitis media is one of the most common reasons practitioners prescribe antibiotics for children. In addition to their antibacterial activity, antibiotics may relieve symptoms quickly and may reduce the chance of residual hearing loss and labyrinthine or intracranial sequelae. However, frequent non-compliance and/or non-adherence to treatment recommendations or regimen by patients or caregivers often results in failure of antimicrobial therapy of otitis media.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 1 is a simplified, schematic, cross-sectional illustration of a human ear showing the drug delivery device and sections of the ear, which are related to the present disclosure;

FIG. 2 is a simplified schematic, cross-sectional illustration showing possible example details and potential operation in accordance with one embodiment of the present disclosure;

DETAILED DESCRIPTION OF EXAMPLE EMBODIMENTS

Overview

Figure 3A:
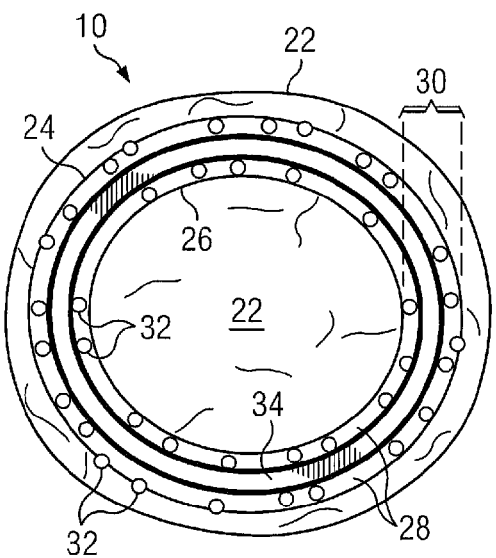
FIG. 3 is a simplified schematic, cross-sectional illustration showing possible example details and potential operation in accordance with another embodiment of the present disclosure.

An apparatus for insertion in an ear, is provided in one example and includes a drug delivery device for insertion into an external auditory canal, wherein the drug delivery device contains one or more pharmaceutically active agents that can be released from the drug delivery device into the external auditory canal. In more particular instances, the drug delivery device can conform to the profile of the external auditory canal. Additionally, the drug delivery device may have a general polymeric matrix structure.

In other implementations, the drug delivery device can have a general shell-like structure. In other examples, the drug delivery device can have a general reservoir structure. In yet other examples, the drug delivery device can have a general cylindrical shape. Additionally, the drug delivery device can have a general annulus shape to allow for sound waves to propagate towards the tympanic membrane. Further the drug delivery device can have a general spiral shape.

In more particular instances, the drug delivery device may be partially or totally impermeable to the pharmaceutically active agents to allow for directional release of pharmaceutically active agents onto target area. In other instances, the drug delivery device can have a first conduit which may be used to deliver pharmaceutically active agents and certain optional additives, including excipients and other active ingredients, to the drug delivery device and a second conduit which may be used to allow for air and other materials escape the drug delivery device. Additionally, the drug delivery device may have at least one element capable of temporary immobilizing the drug delivery device proximate target area.

In other implementations, the apparatus may further include a means for removing the drug delivery device from the ear. In other examples, the drug delivery device may be made of one or more polymers selected from the group of natural polymers, synthetic polymers, swellable polymers, non-swellable polymers, stimuli-responsive polymers, erodible polymers, and non-erodible polymers. In other instances, one or more pharmaceutically active agents may be selected from one or more groups of anti-bacterial agents, anti-viral agents, anti-fungal agents, disinfectant agents, analgesics, anti-inflammatory agents, immuno-suppressive agents, cerumenolytic agents, vestibular agents, and pre-medication agents.

Further, the drug delivery device can contain one or more additives selected from the group of dissolution agents, emulsifying agents, chelating agents, preservatives, cerumenolytic agents, and penetration enhancers. In other examples, the pharmaceutically active agents and additives are incorporated in the polymeric matrix. Also, the formulation of pharmaceutically active agents and additives may be a viscous solution formulation, a suspension, a gel formulation, a paste formulation, an ointment formulation, a cream formulation, a pressed powder formulation, or a tablet formulation. Additionally, the drug delivery device may be inserted into the external auditory canal and positioned proximate tympanic membrane. In other instances, the drug release from the drug delivery device may be controlled by environmental changes in temperature, pH, or ionic strength.

Example Embodiments

Turning to FIG. 1, FIG. 1 is a simplified schematic illustration of a drug delivery device 10 for treating ear disorders. FIG. 1 includes ear 12. Ear 12 includes an external ear portion 14, a middle ear portion 16, and an inner ear portion 18. External ear portion 14 includes an auricle or pinna (the visible part of the ear) and an external auditory canal 20, which ends medially at a tympanic membrane 22. Drug delivery device 10 may be located anywhere inside external auditory canal 20. In an embodiment, drug delivery device 10 may be located proximate to tympanic membrane 22. In another embodiment, drug delivery device 10 may be located in external auditory canal 14.

Drug delivery device 10 may comprise a series of generally circular or oval drug delivery devices designed to fit an inner diameter of external auditory canal 20 and allow for delivery of pharmaceutically active agents to desired sites in the ear to treat external, middle, and/or inner ear disorders, and/or regional or systemic disorders, and/or to alleviate symptoms thereof. In some embodiments, drug delivery device 10 has an annulus shape, which may conform to a profile of external auditory canal 20. In addition to pharmaceutically active agents, drug delivery device 10 may contain additives, including but not limited to, dissolution agents, emulsifying agents, chelating agents, preservatives, cerumenolytic agents, and penetration enhancers, alone or in combination with each other, to facilitate incorporation pharmaceutically active agent within a polymeric matrix or formulation, its release thereof, and its penetration and entry into target areas. In an embodiment, an annulus-shaped drug delivery device 10 may also allow for sound waves propagation towards the eardrum.

For purposes of illustrating certain example techniques of drug delivery device 10, the following foundational information may be viewed as a basis from which the present disclosure may be properly explained.

External ear 14 is composed of an auricle or pinna (the visible part of the ear) and an external auditory canal 20. The lateral portion of the canal is cartilaginous and is covered by thick skin that contains hair follicles and cerumen (earwax)-secreting glands; cerumen may protect the epithelium and may capture foreign particles entering the ear. The medial portion of external auditory canal 20 is bony and covered by squamous (scale-like) epithelium without hair follicles or cerumen glands.

Middle ear 16 consists of tympanic membrane (eardrum) 22, an air-filled tympanic (middle ear) cavity behind it, and three linked ossicles (small bones): the malleus (hammer), incus (anvil), and stapes (stirrup). The malleus is attached to the medial surface of tympanic membrane 22, while the stapes makes contact with the inner ear via the bony stapes footplate at the oval window. The lining of the middle ear is a mucus-secreting epithelium similar to that which lines the nose. The middle ear communicates with the nose via the eustachian tube, a narrow channel that connects the middle ear with the naso-pharynx. Patency of the eustachian tube may allow drainage of secreted mucus and may assure equal pressure on either side of the tympanic membrane, which may facilitate transmission of sound from the tympanic membrane to the oval window.

Inner ear 18 is encased in a very hard bone (the otic capsule) and is filled with fluid. It consists of a sensory organ for hearing (cochlea) and a sensory organ for balance (vestibular labyrinth). Nerves from the cochlea and labyrinth unite to form the acoustic nerve (VIII), which runs through the bony internal auditory canal in the temporal bone to the brainstem.

Acute otitis media, or infection of the middle ear, usually accompanies an upper respiratory infection. Symptoms include pain, often with systemic symptoms such as fever, nausea, vomiting, and diarrhea. Some patients may also describe unilateral hearing impairment. Diagnosis is based on otoscopy—a visual inspection of the ear and eardrum, also known as tympanic membrane—which may show a bulging, erythematous tympanic membrane with indistinct landmarks and displacement of the light reflex. Spontaneous perforation of the tympanic membrane may cause serosanguineous or purulent discharge from the ear, known as otorrhea. In general, etiology of acute otitis media may be bacterial or viral—the latter is often complicated by secondary bacterial infection.

When used properly, ototopical antibiotic preparations used to treat acute otitis media may be more effective and safer than systemic antibiotic preparations. The most commonly used ototopical preparations are drops, which are available as single agents or as combination products. Single agent antibiotic eardrops are usually available as solutions having very low viscosities, approaching that of water. Combination products, on the other hand, tend to be more viscous because they are usually dispensed as suspensions. Ototopical treatment may require the patient to lie down or tilt the head so that the infected ear faces up. The earlobe is pulled up and back (in adults) or down and back (in children) to straighten the ear canal. Medicine is then dropped into the ear canal after which the patient may be asked to keep the ear facing up for about 5 minutes to allow for the medicine to coat the ear canal and the lateral surface of the tympanic membrane. Ear drop dosing regimen is drug-dependent and varies in range from 3-10 drops, 2-4 times a day, for 7-10 days.

To be effective, ear drops need to reach and stay in direct contact with the affected area (e.g., tympanic membrane—in case of otitis media) for a certain period of time known as residence time. Quite often, however, ear drops fail to reach the target area, due to either improper administration or inadequate head tilting. Also, eardrops may not fully exert their antimicrobial effect on target area due to a shorter residence time, which may be due, in part, to lack of patient cooperation during and/or after ototopical drop administration. In addition, frequent and long-term dosing regimen (see above) and running of eardrops out of the external auditory canal may contribute to failure of eardrop treatment.

Noncompliance with antibiotic treatment, administered either orally or ototopically, is a frequent occurrence with acute otic infections, a fact which may lead to bacterial resistance to antibiotic treatment in patients who do not complete their course of treatment. Non-compliance is usually due to limitations linked to either the drug itself, the additives, and/or the formulation mode of administration. Limitations linked to systemic drug administration may include drug-related side effects such as gastrointestinal complications and rash, and infrequent dosing, which may also lead to development of bacterial resistance to antibiotic treatment. Limitations linked to ototopical drug administration may include improper dosing technique and dosing variability—which may be due to difficulty in dispensing precise amounts of viscous drops. Other limitations linked to ototopical drug administration may include pain and ototoxicity.

In accordance with one example of implementation of the present disclosure, drug delivery device 10 may substantially resolve most of the aforementioned issues associated with delivery of a pharmaceutically active agent or agents to a target area such as the tympanic membrane. By inserting drug delivery device 10 into an ear of a patient proximate target area, pharmaceutically active agent or agents may be delivered to target area without active assistance from the patient. Such a drug delivery system, which may be applied only once, is aimed at reducing potential risk of complications associated with patient's or caregiver's noncompliance with a treatment program.

In some embodiments of the present disclosure, drug delivery device 10 may be composed of non-eroding polymers containing diffusible pharmaceutically active agents in one or more polymeric matrices. Pharmaceutically active agents may be physically entrapped, post-polymerization, in the polymeric matrix by absorption from a pharmaceutically active agent solution, or during manufacturing of the polymeric system. Alternatively, it may be chemically bound to the polymeric matrix. Drug release may be accomplished by, but not limited to, simple diffusion, facilitated diffusion, osmosis, hydrolysis, or enzymatic cleavage from the polymer.

Certain embodiments of the present disclosure may possess elements responsive to local disease modifiers and/or micro-environmental changes, including but not limited to, change in temperature, pH or osmolarity—modifiers and changes that can be used to control drug release from the polymeric matrix or formulation. An example for such a need for a self-controlled release of pharmaceutically active agent may be when there is a need for an initial enhanced drug release (burst effect)—which may be triggered by an elevated local temperature, which may result from an acute phase of the disease—followed by a slower pharmaceutically active agent release rate (maintenance drug release), when temperature subsides.

In other embodiments of the present disclosure, drug delivery device 10 may be composed of non-eroding polymers shaped as reservoir and having at least one portion which is made of polymeric membrane, which is permeable to pharmaceutically active agents. The pharmaceutically active agents and additives, contained within the reservoir, may be in a form of, but not limited to, solution or suspension. Drug release from the reservoir-based drug delivery device may be accomplished by, but not limited to, simple diffusion, facilitated diffusion, osmosis, hydrolysis, or enzymatic cleavage from the molecular moieties contained in the reservoir.

In some embodiments of the present disclosure, drug delivery device 10 may be made of one or more biodegradable polymers where pharmaceutically active agent moiety may be incorporated into the polymeric matrix during or post polymerization. Preferably, homogeneous surface erosion of the polymeric matrix, may be designed to coincide with preferred release profile of pharmaceutically active agents.

Certain embodiments of the present disclosure may be based on eroding polymers having partial non-eroding, non-contracting, impermeable or semi-permeable membranes (collectively, "limiting membrane"). In these cases, erosion and drug release may occur only opposite to the limiting membrane. Functions of the limiting membrane may include: (a) maintenance of device shape and therefore proper localization in proximity of target area, (b) provision of unidirectional release of pharmaceutically active agent opposite limiting (impermeable) membrane, and/or (c) control of flux of pharmaceutically active agent through the limiting (semi-permeable) membrane.

In an embodiment, drug delivery device 10 may be composed of non-eroding polymers containing diffusible pharmaceutically active agents in matrix with the polymer. Pharmaceutically active agents may be incorporated throughout the polymeric matrix either by absorption or diffusion from a pharmaceutically active agent solution or via incorporation of the pharmaceutically active agent (liquid or solid particles) during manufacturing of the polymeric device. Alternatively, the pharmaceutically active agents may be chemically bound to polymeric matrix. Release of pharmaceutically active agent or agents may be accomplished by, but not limited to, diffusion, hydrolysis, enzymatic cleavage, or a combination thereof.

In another embodiment, drug delivery device 10 may be a device made of porous, swellable, non-biodegradable, matrix polymer having various absorption capacities. Loading of pharmaceutically active agent or agents into the polymeric matrix may be accomplished by soaking the polymeric matrix in a pharmaceutically active agent solution, for a certain period of time, which may cause the polymer to swell. The polymer swollen status substantially may remain in effect as long as it is stored in a pharmaceutically active agent solution or in a suitable packaging system. Upon insertion into the external auditory canal, the pharmaceutically active agent may be released from the polymeric matrix by shrinking the polymeric matrix and reducing its swollen shape.

Representative materials, which may be used to construct the various elements of embodiments of drug delivery device 10, may include, but are not limited to, components selected from the lists below, used either alone or in combination with one or more materials from the same group or other groups. Also, the process of fabrication, formulation, and making of all polymeric matrices and other formulations, according to various embodiments of the present disclosure, including but not limited to, pharmaceutically active agent incorporation and release thereof are consistent with common and well known methods while using the materials described in the present document and others, which may be commonly used in the art.

Substantial non-swellable, non-contractible, non-eroding components, which may be used in certain embodiments of the present disclosure, may include, but are not limited to, polyacrylics, polystyrenes, polyethylenes, polypropylenes, polycarbonates, polyimides, poly-etheretherketone, parylene, polyvinylchloride, polytetrafluoroethylene, polyethylene vinyl acetate, polyethylene terephthalate, and polyurethane.

Substantial swellable, non-eroding materials, which may be used in certain embodiments of the present disclosure, may include, but are not limited to, acrylic hydrogel polymers, silicones, rubbers, styrene-butadiene, polyisoprene, polyisobutylene, and certain polyesters and polyamides.

Synthetic and/or semi-synthetic polymers, which may be used in certain embodiments of the present disclosure, may include, but are not limited to, thermoplastic elastomers, including but not limited to, silicone elastomers, styrene block copolymers, thermoplastic copolyesters, thermoplastic polyamides, thermoplastic polyolefins, thermoplastic polyurethanes, thermoplastic vulcanizates, polyvinyl chloride, polyaminoacids and their derivatives, fluoropolymers including, but not limited to, polytetrafluoroethylene, fluorinated ethylene propylene, ethylene/tetrafluoroethylene copolymer, perfluoroalkoxy, polyurethane, polycarbonate, silicone, acrylic compounds, thermoplastic polyesters, polypropylene, polyethylene, nylon, and sulfone resins.

Substantial natural polymers, which may be used in certain embodiments of the present disclosure, may include, but are not limited to, cellulose polymers, collagen, starch blends, hyaluronic acid, alginates, and carrageenan.

Substantial stimuli responsive polymers are polymers, which undergo strong conformational changes following environmental changes (e.g., pH, temperature, ionic strength). These changes result in phase separation from aqueous solution or changes in hydrogel size. For example, shrinking and concurrent release of pharmaceutically active agent or agents may be triggered and/or enhanced (burst effect) by an increase in tissue temperature, as often seen in otitis externa or otitis media. When the high temperature subsides, release of pharmaceutically active agent may be slow (maintenance level).

Substantial thermal responsive polymers, which may be used in certain embodiments of the present disclosure may include, but not limited to, poly(N-substituted acrylamide) family such as poly (N-isopropylacrylamide) (PNIPAAm), poly(N,N'-diethyl acrylamide), poly (dimethyl-aminoethyl methacrylate), poly(N-(L)-(1-hydroxymethyl) propylmethacrylamide) poly (NIPAAm-co-butyl methacrylate) (poly (NIPAAm-co-BM) as well as pluronics or poloxamers (PEO-PPO-PEO), which undergo changes in hydrophobic associations of PPO blocks leading to the substantial formation of micelle structures above critical micelle temperature.

Substantial pH-Responsive Polymers, which may be used in certain embodiments of the present disclosure, may include, but are not limited to, those with anionic groups like polycarboxylic acids as polyacrylic acid or polymethacrylic acid, polyacidic polymers such as polysulfonamides (derivatives of p-aminobenzenesulfonamide), and cationic polyelectrolytes such as poly(N,N-diakyl aminoethyl methacrylates), poly(lysine), poly(ethylenimine), and chitosan.

Substantial erodible polymers into which the pharmaceutically active agent or agents may be incorporated and released, which may be used in certain embodiments of the present disclosure, may include, but are not limited to, polyorthoesters, polyphosphazenes, poly-anhydrides, polyarylates, and poly-phospho-esters, polylactide and polyglycolide and block co-polymer variations of those with other polymer groups such as polyethylene glycol or polyoxyethylene.

Cross-linking agents may be used to construct the polymeric matrix of drug delivery device 10. Representative substantial cross-linking agents, which may be used in certain embodiments of the present disclosure, may include, but not limited to, agents from the following list, in part or in their entirety, alone or in combination with other agents. N-Hydroxy-sulfosuccinimide sodium salt; Nitrilotriacetic acid tri(N-succinimidyl) ester; 4-Azidophenyl isothiocyanate; isooctyl 3-mercaptopropionate; and 1,4-Bis(acryloyl) piperazine, N-(3-Dimethyl-aminopropyl)-N-ethylcarbodiimide hydrochloride.

Drug delivery device 10 may be configured to deliver pharmaceutically active agents, which may include, but are not limited to, anti-bacterial agents, anti-viral agents, anti-fungal agents, disinfectant agents, analgesics, anti-inflammatory agents, immuno-suppressive agents, cerumenolytic agents, vestibular agents, and premedication agents. Pharmaceutically active agent may be incorporated in drug delivery device 10 either alone or in combination with agents from the same group or one or more other groups and/or additives.

Representative substantial anti-bacterial agents, which may be used in certain embodiments of the present disclosure, may include, but are not limited to, natural penicillins such as penicillin, aminopenicillins such as amoxicillin and ampicillin, beta-lactamase inhibitors such as amoxicillin and clavulanate, macrolides such as erythromycin, azithromycin, and clarithromycin, first generation cephalosporins such as cephalexin, second generation cephalosporins such as cefaclor and cefuroxime, third generation cephalosporins such as cefdinir, ceftazidime, ceftriaxone, and cefixime; anti-infectives, quinolons and fluoroquinolons such as olofloxacin, ciprofloxacin, moxifloxacin, levofloxacin, and gatifloxacin alone or in combinations with other agents or in combination with additives and/or steroids such as dexamethasone, such as in ciprofloxacin/dexamethasone and hydrocortisone, such as in hydrocortisone/neomycin/polymyxin b, sulfonamides such as sulfisoxazole alone or in combination with other drugs such as sulfamethoxazole/trimethoprim, or miscellaneous otic agents such as antipyrine/benzocaine/phenylephrine. The agents incorporated in the drug delivery device either alone or in combination with other agents and/or additives.

Representative substantial analgesic agents, which may be used in certain embodiments of the present disclosure, may include, but are not limited to, benzocaine, acetaminophen, and ibuprofen, alone or in combination with other agents and/or additives.

Representative substantial cerumenolytic agents, which may be used in certain embodiments of the present disclosure, may include, but are not limited to, carbamide peroxide and triethanolamine polypeptide oleate, alone or in combination with other agents and/or additives.

Representative substantial anti-inflammatory agents, which may be used in certain embodiments of the present disclosure, may include, but are not limited to, steroids, such as dexamethasone, and non steroidal anti inflammatory agents such as naproxen, ketoprofen, celecoxib, and indomethacin, alone or in combination with other agents and/or additives.

Representative substantial vestibular suppressants, which may be used in certain embodiments of the present disclosure, may include, but are not limited to, agents from the groups of anticholinergics, antihistamines, and benzodiazepines and a combination thereof. Examples of vestibular suppressants are meclizine and dimenhydinate (antihistamine-anticholinergics) and lorazepam and diazepam (benzodiazepines).

Representative substantial additives, which might be incorporated in certain embodiments of the present disclosure may include, but are not limited to, penetration enhancers, preservatives, chelating agents, dissolution agents, emulsifying agents, cerumenolytic agents, alone or in combination with others.

Representative substantial penetration enhancers, which might be incorporated in certain embodiments of the present disclosure may include, but are not limited to, low molecular weight alcohols, such as ethanol and oleyl alcohol, alkyl methanol sulphoxides, N-methyl-2-pyrrolidone, fatty amines such as oleylamine, fatty acids such as oleic acid, palmitoleic acid, linoleic acid, and myristate acid, esters of fatty acids such as isopropyl myristate; gluconic acid and its derivatives such as conolactone (esp., gluconon-D-lactone), azone, and propylene glycol, singly or in combination. Propylene glycol, either alone or in combination with another enhancer, such as oleic acid or ethanol. Gluconolactone, esp., glucono-D-lactone, either alone or in combination with another enhancer, such as propylene glycol.

Representative substantial preservatives, which might be incorporated in certain embodiments of the present disclosure, either alone or in combination with others, may include, but are not limited to, water soluble compounds, which may function also as antimicrobials, such as benzethonium salt, e.g., benzethonium chloride. Alkanolamine chloride, sulfate, phosphate, salts of benzoic acid, acetic acid, salicylic acid, oxalic acid, phthalic acid, gluconic acid, 1-naphthalenesulfonic acid, 2-naphthalenesulfonic acid, tartaric acid, propionic acid, ascorbic acid, mandelic acid, malic acid, citric acid, triethanolammonimum chloride, triethanoammonium dihydrogen phosphate, triethanolammonium sulfate, sodium benzoate, potassium benzoate, ammonium benzoate, sodium acetate, potassium salicylate, ammonium salicylate, sodium oxalate, potassium oxalate, ammonium phthalate, sodium gluconate, potassium gluconate, ammonium gluconate, ammonium 1-naphthalenesulfonate, potassium 2-naphthalenesulfonate, ammonium 2-naphthalenesulfonate, sodium 2-naphthalenesulfonate, potassium tartarate, sodium maleate, potassium maleate, sodium malonate, sodium succinate, sodium fumarate, sodium propionate, triethanolammonium proptionate, sodium ascorbate, triethanolammonium ascorbate, potassium ascorbate, sodium mandelate, sodium malate, sodium citrate, potassium citrate, and triethanolammonium citrate.

Representative substantial chelating agents, which might be incorporated in certain embodiments of the present disclosure may include, but are not limited to, disodium ("EDTA"), edentate trisodium, edentate tetrasodium, or diethylene-amine pentaacetate.

Pharmaceutically active agents may be substantially incorporated into polymeric drug delivery systems at various loading ratios. The upper limit for maximum loading of pharmaceutically active agents may be reached when there may be disruption of polymer structural integrity. This usually occurs at loading levels above 50-60% by weight. Typically loading in polymers may be achieved at levels of 30-40%. Incorporation of pharmaceutically active agents into polymers can be achieved during polymerization or soaked into the polymer following its polymerization. Note that the above and below example estimates and calculations are provided for illustration purposes only. The examples provided should not limit the scope or inhibit the broad teachings of explicit or implied drug delivery device formulation, shape, design, mode of drug absorption, release, or delivery properties of any embodiment, which may be directly or indirectly derived from the present disclosure. For example, in normal humans, the total ear canal volume ranges from 0.3 ml to 1.0 ml in children, and from 0.65 to 1.75 ml in adults. During disease state such as otitis media, the volume may increase to as much as 2.9 ml. Therefore, total drug volume at 40% loading might range from about 0.12 ml to as high as 1.2 ml. Assuming a density of 1.0 g/ml, the total maximum drug weight at that loading ratio may therefore be approximately 1.2 g. Assuming a cylindrical shaped drug delivery device—which has a central cylindrical void, or tunnel, to allow for sound waves to propagate towards the eardrum—the maximum loaded drug would be 0.6 g to achieve a volume equal to 50% of the external auditory canal.

Rate of release of pharmaceutically active agents may be substantially controlled by, but not limited to, one or more of the following: the total load of pharmaceutically active agent, composition of the polymeric matrix or formulation, type and density of cross-linker(s), volume, shape and surface area of the drug delivery system, and external/environmental stimuli (such as temperature or pH)—designed to control swelling or shrinking of the polymeric matrix, increase or decrease viscosity, or otherwise release pharmaceutically active agents from the polymeric matrices or formulations. Based on the potency of the pharmaceutically active agent, need for burst effect, and desired release duration of the pharmaceutically active agent—release rates of pharmaceutically active agents may be designed to range from nanograms to milligrams per day. In the drug loading calculation example above, where the maximum 0.6 g of pharmaceutically active agent may be loaded in the device, a release rate of 3.25 mg/day would allow for approximately 6 months worth of delivery, which is about 18 times the conventional 10-day maximum duration of treatment. This should afford potential great flexibility in choice of components for desired drug delivery systems and flexibility in drug loading levels and drug release rates from the drug delivery systems.

Once otitis externa (i.e., infection of the external ear) or otitis media is suspected, the physician may inspect the patient's external auditory canal and tympanic membrane for signs of inflammation, infection, or effusion and may gently clean the external auditory canal from accumulated cerumen and other debris, using thin-threaded soft cotton swabs. An otic drug delivery system, selected from a group of embodiments of the present disclosure, stored either in a suitable packaging device or in a pharmaceutically active agent solution, the latter contained either in a stand-alone container or in a prefilled device applicator, may be placed, under direct otoscopy, anywhere in the external auditory canal (to substantially treat otitis externa) or in proximity of the tympanic membrane (to substantially treat otitis media), and may be left there for a recommended duration of time specific for the pharmaceutically active agent or agents in use. A the end of the specified period, otoscopy may be performed again to inspect the ear and the position and status of the inserted drug delivery device following which the drug delivery device may be slowly removed from the patient's external auditory canal using a dressing forceps or a similar tool to hold the drug delivery system, or the drug delivery system's extraction or tethering means, and pull it out of the patient's ear. Similar approach may be taken to apply and remove other drug delivery device embodiments of the present disclosure, which may be aimed at ototopically treating vestibular, regional, or systemic disorders.

Turning to FIG. 2A, FIG. 2A is a simplified cross-sectional schematic illustration showing one possible set of details and potential operation associated with drug delivery device 10 of an embodiment of the present disclosure. Drug delivery device 10 may be a non-contracting, generally O-ring shaped or oval shaped polymeric matrix-based device designed to fit inside an external auditory canal. Drug delivery device 10 has an outside diameter, which fits the inside diameter of the external auditory canal, and an inside diameter (hole), which may allow for sound waves to reach the tympanic membrane. Drug delivery device 10 has a radial cross-section 30, an outer area 24 and inner area 26. Outer area 24 and inner area 26 combine to form the entire envelope surface area of polymeric matrix 28. Contained within polymeric matrix 28 may be one or more pharmaceutically active agents 32. Pharmaceutically active agents 32 may be combined with other agents and additives, all of which may be physically entrapped in and/or chemically bound to polymeric matrix 28.

In use, drug delivery device 10 may be stored in a pharmaceutically active agent solution or a suitable packaging system from which it may be removed and inserted anywhere along the external auditory canal 20 or in proximity of tympanic membrane 22. Drug delivery device 10 may be inserted by using forceps, another similar tool, or an insertion applicator specifically designed for insertion of drug delivery device 10.

As shown in FIG. 2B, pharmaceutically active agents 32 may be released from polymeric matrix 28 by diffusion, hydrolysis, or enzymatic cleavage onto or near tympanic membrane 22 and onto or near adjacent walls of external auditory canal 20. Subsequently, pharmaceutically active agents 32 may diffuse through the tympanic membrane and enter middle ear 16.

FIG. 3A is a simplified cross-sectional schematic illustration showing another possible set of details and potential operation associated with drug delivery device 10 of an embodiment of the present disclosure. In the embodiment of FIG. 3, drug delivery device 10 has an outside diameter, which fits the inside diameter of the external auditory canal and an inside diameter (hole), which may allow sound waves to reach the tympanic membrane. Drug delivery device 10 has a radial cross-section 30, an outer area 24 and an inner area 26. Outer area 24 and inner area 26 combine to form the entire envelope surface area of polymeric matrix 28, which surrounds supporting element 34. Contained within polymeric matrix 28 may be one or more pharmaceutically active agents 32. Pharmaceutically active agents 32 may be combined with other agents and additives, all of which may be physically entrapped in and/or chemically bound to polymeric matrix 28.

Figure 3B:
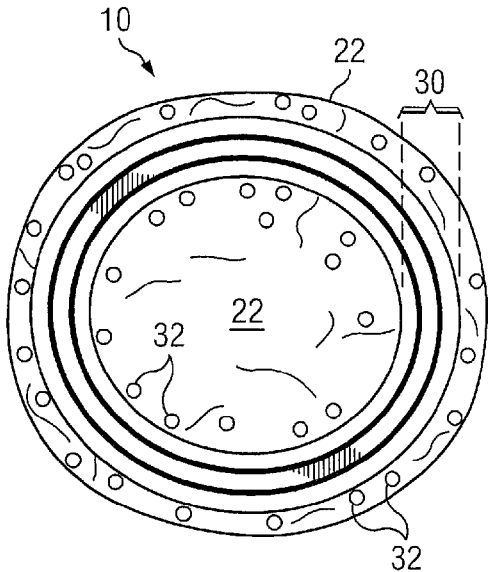

As shown in FIG. 3B, pharmaceutically active agents 32 may be released from polymeric matrix 28 by diffusion, hydrolysis, or enzymatic cleavage onto or near tympanic membrane 22 and onto or near adjacent walls of external auditory canal 20. Further, pharmaceutically active agents 32 may diffuse through tympanic membrane 22 and enter middle ear 16.

Figure 4:
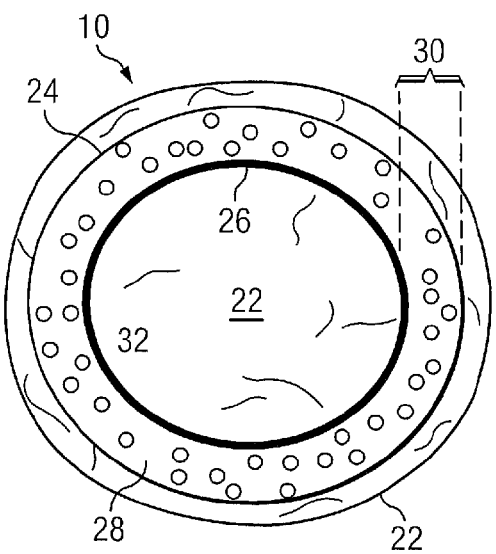
FIG. 4 is a simplified schematic, cross-sectional illustration showing possible example details and potential operation in accordance with yet another embodiment of the present disclosure.

FIG. 4 is a simplified cross-sectional schematic illustration showing yet another possible set of details and potential operation associated with an embodiment of the present disclosure. FIG. 4 includes drug delivery device 10. Drug delivery device 10 has an outside diameter, which fits the inside diameter of the external auditory canal, and an inside diameter (hole), which may allow sound waves to reach the tympanic membrane. Drug delivery device 10 has a radial cross-section 30, an outer area 24 and an inner area 26. Outer area 24 and inner area 26 combine to form the entire envelope surface area of polymeric matrix 28. Contained within polymeric matrix 28 may be one or more pharmaceutically active agents 32. Pharmaceutically active agents 32 may be combined with other agents and additives, all of which may be physically entrapped in and/or chemically bound to polymeric matrix 28. Inner area 26 may include an impermeable or semi-permeable, non-contracting, membrane, which may serve as a barrier for inward release of pharmaceutically active agents and additives. Inner area 26 may prevent or reduce the release of pharmaceutically active agents 32 and additives thereby directing their release peripherally through outer area 24, onto or near the adjacent walls of external auditory canal 20 and/or periphery of tympanic membrane 22.

Figure 5:
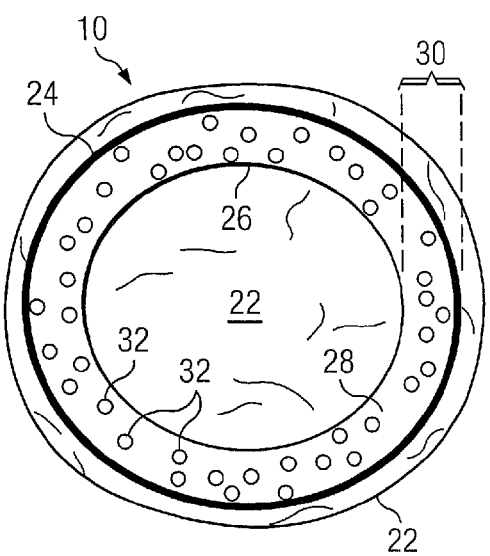
FIG. 5 is a simplified schematic, cross-sectional illustration showing possible example details and potential operation in accordance with still another embodiment of the present disclosure.

FIG. 5 is a simplified cross-sectional schematic illustration showing still another possible set of details and potential operation associated with an embodiment of the present disclosure. FIG. 5 includes drug delivery device 10. Drug delivery device 10 has an outside diameter, which fits the inside diameter of the external auditory canal and an inside diameter (hole), which may allow sound waves to reach the tympanic membrane. Drug delivery device 10 has a radial cross-section 30, an outer area 24 and an inner area 26. Outer area 24 and inner area 26 combine to form the entire envelope surface area of polymeric matrix 28. Contained within polymeric matrix 28 may be one or more pharmaceutically active agents 32. Pharmaceutically active agents 32 may be combined with other agents and additives, all of which may be physically entrapped in and/or chemically bound to polymeric matrix 28. Outer area 24 may include an impermeable or semi-permeable, non-contracting membrane, which may serve as a barrier for outward release of pharmaceutically active agents and additives. Outer area 24 may prevent or reduce the release of pharmaceutically active agents 32 and additives thereby directing their release centrally, onto or near tympanic membrane 22.

Figure 6:
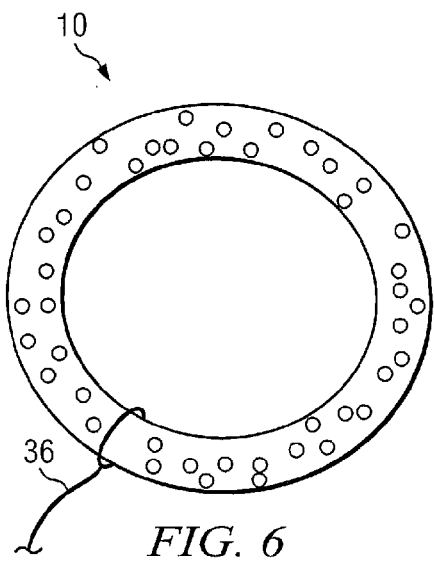
FIG. 6 is a simplified schematic cross-sectional illustration showing possible example details and potential operation in accordance with one or more embodiments of the present disclosure.

FIG. 6 is a simplified cross-sectional schematic illustration showing yet still another possible set of details and potential operation associated with certain embodiments of the present disclosure. FIG. 6 includes drug delivery device 10 with a tethering or extraction means 36. Extraction means 36 may be secured to drug delivery device 10 such that when extraction means 36 is pulled, drug delivery device 10 may be removed from the ear.

Figure 7A:
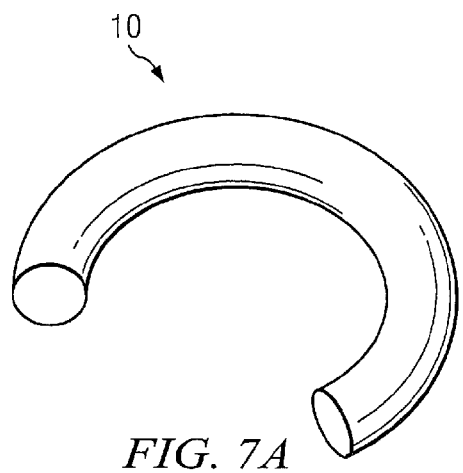
FIG. 7A is a simplified, tridimensional schematic illustration showing possible example details and potential operation of possible additional embodiments of the present disclosure.
Figure 7B:
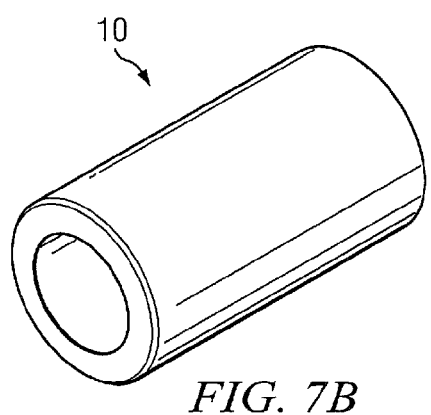
FIG. 7B is a simplified, tridimensional schematic illustration showing possible example details and potential operation of possible additional embodiments of the present disclosure.
Figure 7C:
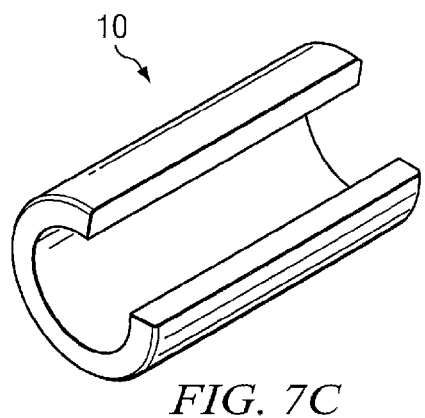
FIG. 7C is a simplified, tridimensional schematic illustration showing possible example details and potential operation of possible additional embodiments of the present disclosure.
Figure 7D:
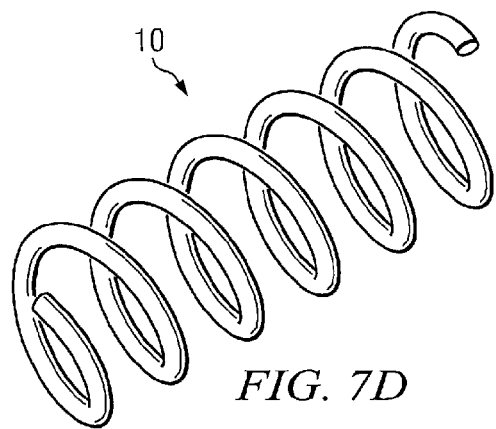
FIG. 7D is a simplified, tridimensional schematic illustration showing possible example details and potential operation of possible additional embodiments of the present disclosure.

FIGS. 7A-7D illustrate different schematic tridimensional embodiments of drug delivery device 10. FIG. 7A illustrates a generally open ring-like shape of drug delivery device 10. One advantage of the generally open ring-like shape of drug delivery device 10 may be its spring-like potential action such that when squeezed it facilitates insertion in the external ear canal, and when released, post-insertion, it allows for the immobilization of drug delivery device 10 proximate target area by creating adequate peripheral pressure on the walls of the external auditory canal. FIG. 7B illustrates a flexible cylindrical or sleeve-shaped drug delivery device 10. The cylinder or sleeve shape may provide greater surface area for loading of pharmaceutically active agents 32 and additives. In addition, the cylindrical shape of drug delivery device 10 may provide a large surface area proximate walls of external auditory canal 20 allowing more effective release of pharmaceutically active agents 32 proximate target area, especially in cases of otitis externa or combined cases of otitis externa and otitis media. FIG. 7C illustrates a generally open semi-cylinder- or semi-sleeve-shaped drug delivery device 10. The generally open semi-cylinder or semi-sleeve shape of drug delivery device 10 combines the advantages described for the embodiments described in FIGS. 7A and 7B—namely spring-like action and larger drug loading and release surface area. FIG. 7D illustrates a spiral-shaped drug delivery device 10, which may provide an even larger surface area for loading and release of pharmaceutically active agents 32 and, in compressed mode, may facilitate insertion to cover a large target area, such as the walls of external auditory canal 20. Note that the embodiments illustrated in FIGS. 7A-7D are shown only as examples and drug delivery device 10 is not restricted to any one particular profile. Each of the embodiments may have variable lengths and may fit the general inner circumferential shape of the external auditory canal, and possess any of the features described for any of the above described embodiments.

Figure 8A:
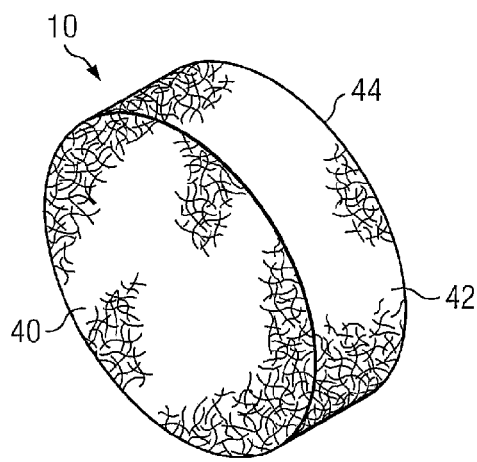
FIG. 8A is a simplified, tridimensional schematic illustration showing possible example details and potential operation in accordance with one embodiment of the present disclosure.
Figure 8B:
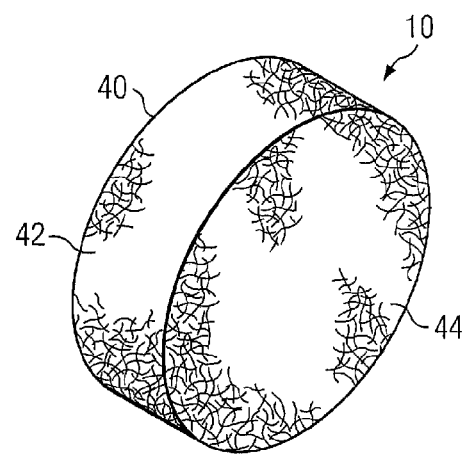
FIG. 8B is a simplified, tridimensional schematic illustration showing possible example details and potential operation in accordance with one embodiment of the present disclosure.

FIGS. 8A and 8B are simplified schematic tridimensional illustrations showing another possible set of details and potential operation associated with embodiments of the present disclosure. FIGS. 8A and 8B illustrate drug delivery device 10 as having a generally flattened cylindrical shape and a circular or oval cross-sectional profile. Drug delivery device 10 includes a lateral surface 40, a circumferential surface 42, and a medial surface 44. In an embodiment, drug delivery device 10 has predetermined diameter and thickness and its polymeric matrix may contain pharmaceutically active agent or agents and additives, which may be physically entrapped in and/or chemically bound to the polymeric matrix. Drug delivery device 10, may be stored in a pharmaceutically active agent solution or in a suitable packaging device from which it may be removed and inserted proximate lateral surface of tympanic membrane 22 (shown in FIG. 1), using common surgical tools, including but not limited to, forceps, or specialized insertion applicators. Pharmaceutically active agent or agents and additives may then be released from the polymeric matrix of the drug delivery device 10 by diffusion, hydrolysis, or enzymatic cleavage onto surrounding tissues and tympanic membrane 22 through which it diffuses to middle ear 16.

Figure 9A:
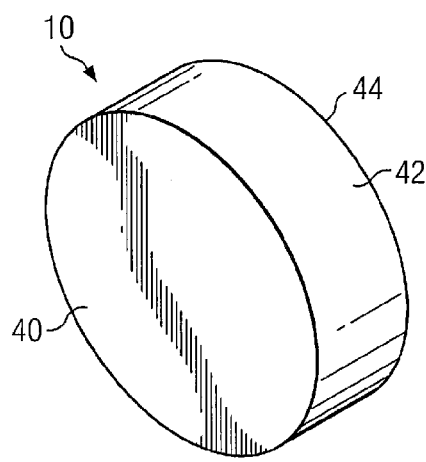
FIG. 9A is a simplified, tridimensional schematic illustration showing possible example details and potential operation in accordance with another embodiment of the present disclosure.
Figure 9B:
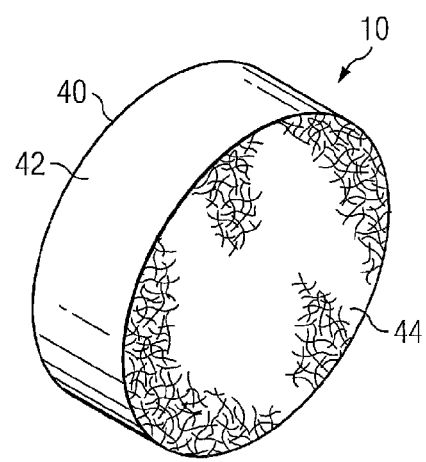
FIG. 9B is a simplified, tridimensional schematic illustration showing possible example details and potential operation in accordance with another embodiment of the present disclosure.

FIGS. 9A and 9B are simplified schematic tridimensional illustrations showing yet another possible set of details and potential operation associated with embodiments of the present disclosure. FIGS. 9A and 9B illustrate drug delivery device 10 as having a generally flattened cylindrical shape and a circular or oval cross-sectional profile. Drug delivery device 10 includes a lateral surface 40, a circumferential surface 42, and a medial surface 44. In an embodiment, drug delivery device 10 has one or more surfaces that are permeable or impermeable to the drug and/or additive moieties contained within its polymeric matrix. For example, FIGS. 9A and 9B show drug delivery device 10 with lateral surface 40 and circumferential surface 42 designed to be substantially impermeable surfaces, while medial surface 44 is substantially permeable to the pharmaceutically active agents and/or additives contained within its polymeric matrix. Drug delivery device 10 may have predetermined diameter and thickness and its polymeric matrix may contain pharmaceutically active agent or agents and additives, which may be physically entrapped in and/or chemically bound to its polymeric matrix. Drug delivery device 10 may be stored in a pharmaceutically active agent solution or suitable packaging device from which it may be removed and inserted in the external auditory canal, such that its medial permeable surface is proximate lateral surface of tympanic membrane 22 (Shown in FIG. 1), using common surgical tools, including but not limited to, forceps, or specialized insertion applicators. Pharmaceutically active agent or agents and additives may then be released from the polymeric matrix by diffusion, hydrolysis, or enzymatic cleavage onto tympanic membrane 22 through which they may unidirectionally diffuse and enter the middle ear.

Figure 10A:
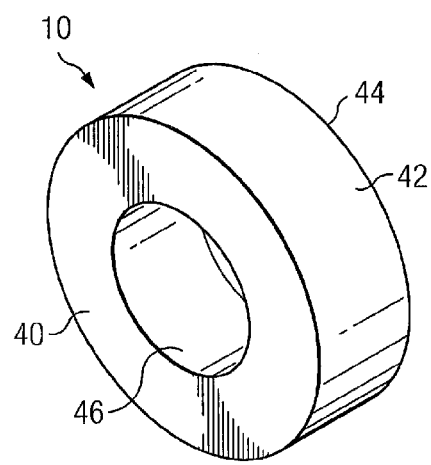
FIG. 10A is a simplified, tridimensional schematic illustration showing possible example details and potential operation in accordance with yet another embodiment of the present disclosure.
Figure 10B:
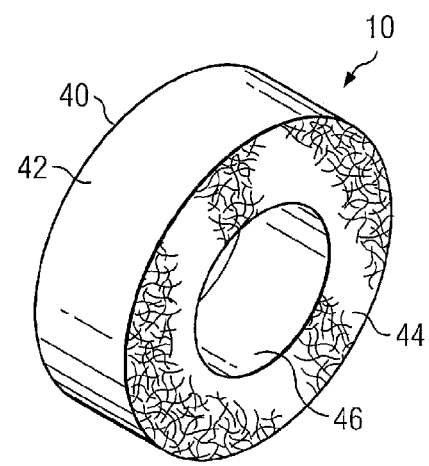
FIG. 10B is a simplified, tridimensional schematic illustration showing possible example details and potential operation in accordance with yet another embodiment of the present disclosure.

FIGS. 10A and 10B are simplified schematic tridimensional illustrations showing still another possible set of details and potential operation associated with embodiments of the present disclosure. FIGS. 10A and 10B illustrate drug delivery device 10 as having a generally flattened O-ring shape and a circular or oval cross-sectional profile. Drug delivery device 10 includes lateral surface 40, outer circumferential surface 42, medial surface 44, and an inner circumferential surface 46, the latter delineating a central space or hole made to allow incoming sound waves to reach tympanic membrane 22. In an embodiment, drug delivery device 10 has one or more surfaces that are permeable or impermeable to the drug and/or additive moieties contained within its polymeric matrix. For example, FIGS. 10A and 10B show that lateral surface 40, outer circumferential surface 42, and inner circumferential surface 46 may be substantially impermeable surfaces to release of pharmaceutically active agents and other moieties contained within its polymeric matrix, while medial surface 44 is substantially permeable. Drug delivery device 10 may have predetermined diameters and thickness and its polymeric matrix may contain pharmaceutically active agent or agents and additives, which may be physically entrapped in and/or chemically bound to the polymeric matrix. Drug delivery device 10 may be stored in a pharmaceutically active agent solution or a suitable packaging device from which it may be removed and inserted in the external auditory canal, such that its medial permeable surface is proximate lateral surface of tympanic membrane 22 (Shown in FIG. 1), using common surgical tools, including but not limited to, forceps, or specialized insertion applicators. Pharmaceutically active agent or agents and additives may then be released from the polymeric matrix of drug delivery device 10 by diffusion, hydrolysis, or enzymatic cleavage onto tympanic membrane 22 through which they may unidirectionally diffuse and enter the middle.

Figure 11A:
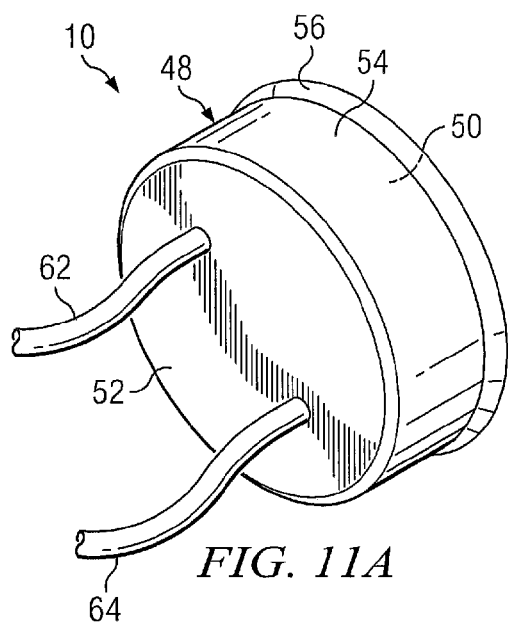
FIG. 11A is a simplified, tridimensional schematic illustration showing possible example details and potential operation in accordance with still another embodiment of the present disclosure.
Figure 11B:
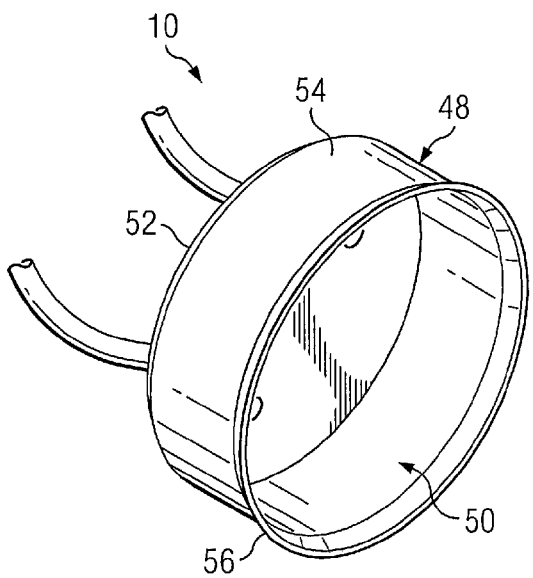
FIG. 11B is a simplified, tridimensional schematic illustration showing possible example details and potential operation in accordance with still another embodiment of the present disclosure.

FIGS. 11A and 11B are simplified schematic tridimensional illustrations showing still yet another possible set of details and potential operation associated with embodiments of the present disclosure. FIGS. 11A and 11B illustrate drug delivery device 10 as having a generally flattened, cylindrically shaped shell 48 and a circular or oval cross-sectional profile. Shell 48 includes lateral surface 52 and outer circumferential surface 54, which are designed to be substantially impermeable to pharmaceutically effective agent and/or additive moieties, which may be contained within cavity 50, which opens medially. The pharmaceutically active agent or agents and additives, may be formulated as, but not limited to, a highly viscous solution, suspension, gel, paste, ointment, wax, cream, pressed powder, or tablet. Cavity 50 may have an outward angled circumferential rim 56, which may contain adhesive and/or may be configured to be attached to tympanic membrane 22 by way of suction (e.g. "suction cup" like effect). Pharmaceutically active agent and additive moieties may be unidirectionally released from cavity 50, through the medial opening of the cavity, by diffusion, hydrolysis, or enzymatic cleavage from molecular entities, which may be contained within the formulation in the cavity, onto tympanic membrane 22. The released pharmaceutically active agent and/or additive moieties may then diffuse through tympanic membrane 22 to enter the middle ear. In one embodiment, shell 48 may contain a first conduit 62 and a second conduit 64. First conduit 62 may be used to deliver pharmaceutically active agent and additive moieties to cavity 50 after drug delivery device 10 has been inserted and positioned proximate tympanic membrane 22. Second conduit 64 may allow air and other material to escape cavity 50 as the drug and additive moieties are delivered into cavity 50.

Figure 12A:
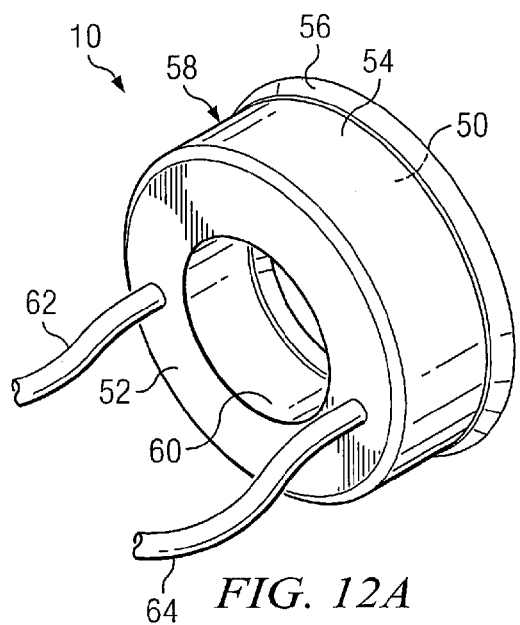
FIG. 12A is a simplified, tridimensional schematic illustration showing possible example details and potential operation in accordance with yet still another embodiment of the present disclosure.
Figure 12B:
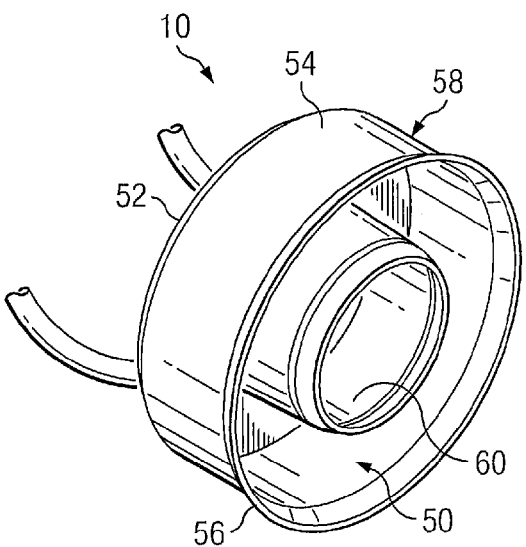
FIG. 12B is a simplified, tridimensional schematic illustration showing possible example details and potential operation in accordance with yet still another embodiment of the present disclosure.

FIGS. 12A and 12B are simplified schematic tridimensional illustrations showing another possible set of details and potential operation associated with embodiments of the present disclosure. FIGS. 12A and 12B illustrate drug delivery device 10 as having a generally flattened O-ring-like or oval shaped shell 58. Shell 58 includes cavity 50, lateral surface 52, outer circumferential surface 54, and inner circumferential surface 60. Surfaces 52, 54, and 60 are designed to be substantially impermeable to the pharmaceutically active agent and/or additive moieties contained within cavity 50. Pharmaceutically active agents and additives within cavity 50 may be formulated as, but not limited to, a highly viscous solution, suspension, gel, paste, ointment, wax, cream, pressed powder, or tablet. Cavity 50 may open medially and have an outward angled circumferential rim 56. Circumferential rim 56 may contain adhesive and/or may be configured to be attached to tympanic membrane 22 by way of suction (e.g. "suction cup" like effect). Pharmaceutically active agent and additive moieties may be released from cavity 50, through the medial opening of the cavity, by diffusion, hydrolysis, or enzymatic cleavage from molecular entities, which may be contained within the formulation in the cavity onto tympanic membrane 22. The released pharmaceutically active agent and/or additive moieties may then unidirectionally diffuse through tympanic membrane 22 to enter the middle ear. In one embodiment, shell 58 may contain first conduit 62 and second conduit 64. First conduit 62 may be used to deliver pharmaceutically active agent and additive moieties to cavity 50 after drug delivery device 10 has been inserted and positioned proximate tympanic membrane 22. Second conduit 64 may allow air and other material to escape cavity 50 as the pharmaceutically active agent and additive moieties are delivered into cavity 50.

Figure 13A:
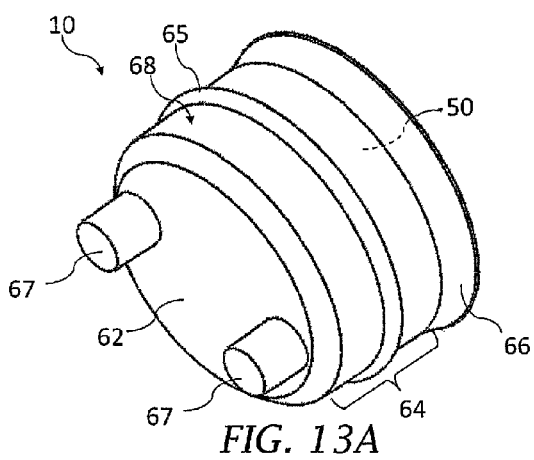
FIG. 13A is a simplified, tridimensional schematic illustration showing possible example details and potential operation in accordance with another embodiment of the present disclosure.
Figure 13B:
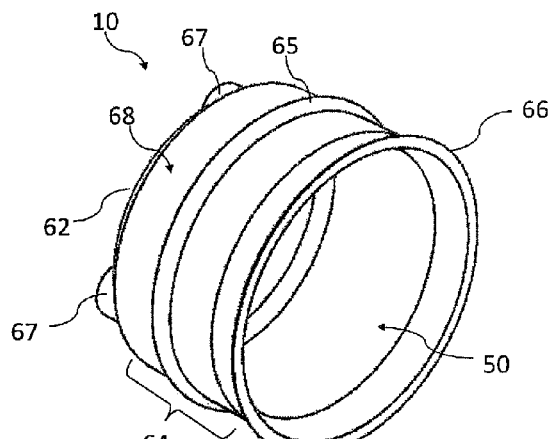
FIG. 13B is a simplified, tridimensional schematic illustration showing another aspect of the embodiment depicted in FIG. 13A.

FIGS. 13A and 13B are simplified schematic tridimensional illustrations showing still yet another possible set of details and potential operation associated with embodiments of the present disclosure. FIGS. 13A and 13B illustrate drug delivery device 10 as having a generally flattened, cylindrically shaped shell 68 and a circular or oval cross-sectional profile. Shell 68 includes lateral surface 62 and outer circumferential surface 64, which are designed to be substantially impermeable to pharmaceutically effective agent and/or additive moieties, which may be contained within cavity 50, which opens medially. Outer circumferential surface 64 may have a protruding circumferential ring 65, which may be used to reinforce device 10 and/or as a stabilizing element fitting snugly in a corresponding groove in a specifically designed device applicator. Cavity 50 may have an outward angled circumferential rim 66, which may contain adhesive and/or may be configured to be attached to tympanic membrane 22 by way of suction (e.g. "suction cup" like effect). The pharmaceutically active agent or agents and additives, contained within cavity 50, may be formulated as, but not limited to, a highly viscous solution, suspension, gel, paste, ointment, wax, cream, pressed powder, or tablet. Pharmaceutically active agent and additive moieties may be unidirectionally released from cavity 50, through the medial opening of the cavity, by diffusion, hydrolysis, or enzymatic cleavage from molecular entities, which may be contained within the formulation in the cavity, onto tympanic membrane 22. The released pharmaceutically active agent and/or additive moieties may then diffuse through tympanic membrane 22 to enter the middle ear. In one embodiment, shell 68 may contain one or more protuberances 67, which may be used as device handles to be grasped with an instrument (e.g., forceps) during insertion and removal of device 10 or as elements that stabilize device 10 within a device applicator.

Figure 14A:
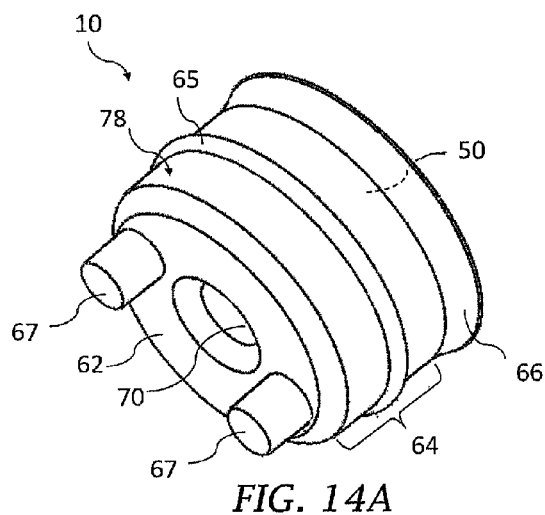
FIG. 14A is a simplified, tridimensional schematic illustration showing possible example details and potential operation in accordance with yet another embodiment of the present disclosure.
Figure 14B:
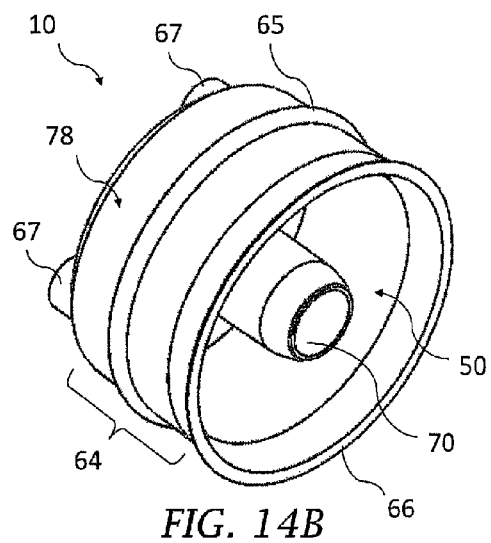
FIG. 14B is a simplified, tridimensional schematic illustration showing another aspect of the embodiment depicted in FIG. 14A.

FIGS. 14A and 14B are simplified schematic tridimensional illustrations showing another possible set of details and potential operation associated with embodiments of the present disclosure. FIGS. 14A and 14B illustrate drug delivery device 10 as having a generally flattened O-ring-like or oval shaped shell 78. Shell 78 includes cavity 50, lateral surface 62, outer circumferential surface 64, and inner circumferential surface 70. Surfaces 62, 64, and 70 are designed to be substantially impermeable to the pharmaceutically active agent and/or additive moieties contained within cavity 50. Outer circumferential surface 64 may have a protruding circumferential ring 65, which may be used to reinforce device 10 and/or as a stabilizing element fitting snugly in a corresponding groove in a specifically designed device applicator. Pharmaceutically active agents and additives within cavity 50 may be formulated as, but not limited to, a highly viscous solution, suspension, gel, paste, ointment, wax, cream, pressed powder, or tablet. Cavity 50 may open medially and have an outward angled circumferential rim 66. Circumferential rim 66 may contain adhesive and/or may be configured to be attached to tympanic membrane 22 by way of suction (e.g. "suction cup" like effect). Pharmaceutically active agent and additive moieties may be released from cavity 50, through the medial opening of the cavity, by diffusion, hydrolysis, or enzymatic cleavage from molecular entities, which may be contained within the formulation in the cavity onto tympanic membrane 22. The released pharmaceutically active agent and/or additive moieties may then unidirectionally diffuse through tympanic membrane 22 to enter the middle ear. In one embodiment, shell 78 may contain protuberances 67 which may be used as device handles to be grasped with an instrument (e.g., forceps) during insertion and removal of device 10 or as elements that stabilize device 10 within a device applicator.

Figure 15:
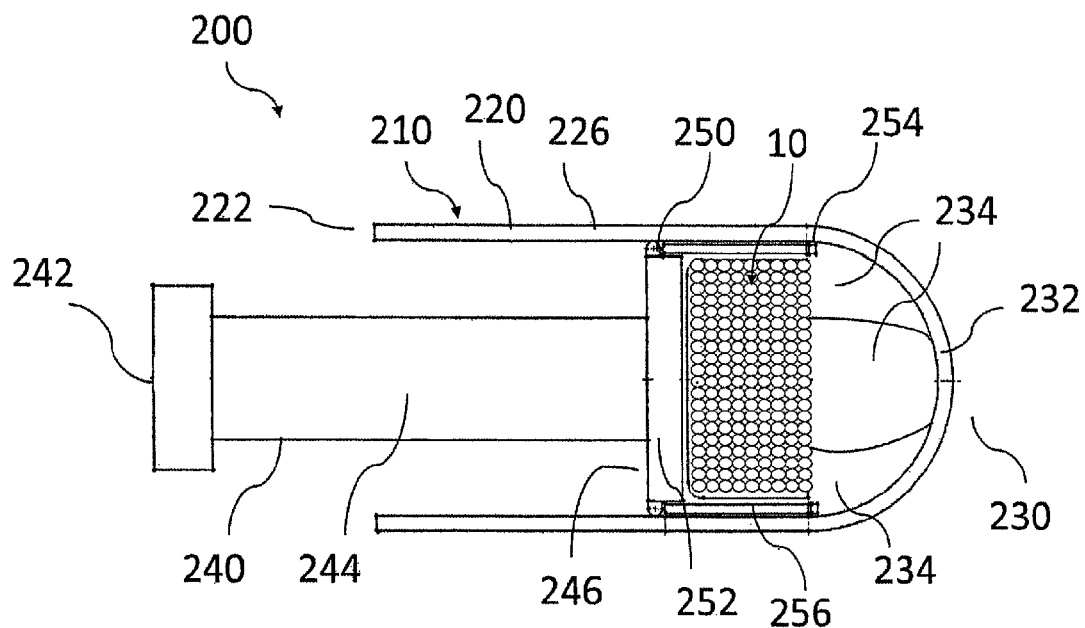
FIG. 15 is a simplified, schematic illustration showing possible example details and potential operation in accordance with one embodiment of an applicator of the present disclosure.
Figure 16:
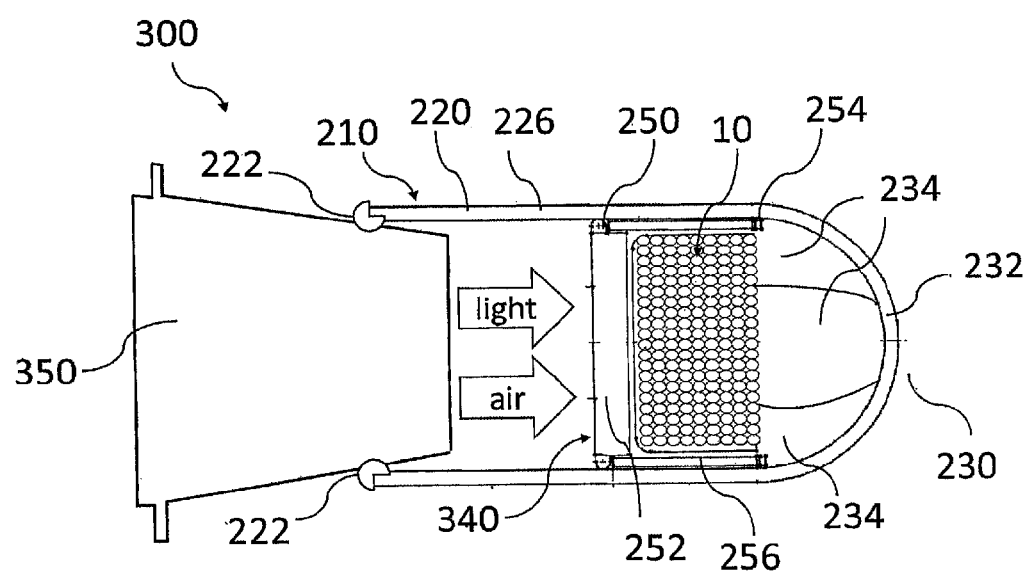
FIG. 16 is a simplified, schematic illustration showing possible example details and potential operation in accordance with another embodiment of an applicator of the present disclosure.

FIGS. 15 and 16 are simplified schematic illustrations showing possible sets of details and potential operation associated with drug delivery device applicator embodiments of the present disclosure.

FIG. 15 is a simplified schematic cross-sectional illustration showing one possible embodiment of drug delivery device applicator 200 of the present disclosure. In this illustration, drug delivery device applicator 200 may have a general cylindrical shape 210 composed of an outer tube-like part 220 and an inner plunger-like part 240. Tube-like part 220, which is designed to smoothly fit within the external auditory canal 20 (FIG. 1) of the human ear, has a proximal end 222, a body 226 and a distal end 230. In one embodiment of the present disclosure, proximal end 222 may have a circular opening leading to a cylindrical cavity within body 226. Distal end 230 of drug delivery device applicator 200 may have a dome-shaped end 232 to facilitate drug delivery device applicator 200 penetration into and insertion along external auditory canal 20. The dome-shaped end 232 is hollow and may be composed of two or more leaflets 234 designed to mechanically open, upon pushing plunger-like part 240, to form a distal circular opening. Plunger-like part 240 has a proximal end 242, medial shaft 244 and a distal end 246. Proximal end 242 is designed to accommodate an operator's thumb to push plunger 240 along the cylindrical cavity of applicator body 226. Distal end 246 of plunger 240 may have a cup-like cradle shape, which may be made of lateral wall 252 and circumferential wall 256, and designed to accommodate drug delivery device 10. In one embodiment of the present disclosure lateral wall 252 and circumferential wall 256 are joined by mechanism 250 that allows their separation when circumferential wall 256 encounters resistance during travel of plunger 240 along cylindrical cavity of body 226. One or more protuberances 254, which may be located proximate or as part of base of leaflets 234 may serve (a) to open the dome 232 at distal end 230 and (b) to block further advancement of circumferential wall 256 of the cup-like cradle thus causing lateral wall 252 to disengage from circumferential wall 256 and move along the opened dome while pushing forward drug delivery device 10 toward tympanic membrane 22.

FIG. 16 is a simplified schematic cross-sectional illustration showing another possible embodiment of drug delivery device applicator 300 of the present disclosure. In this illustration, drug delivery device applicator 300 may have a general cylindrical shape 210 composed of an outer tube-like part 220 and an inner cup-like cradle 340. Tube-like part 220, which is designed to smoothly fit within the external auditory canal 20 (FIG. 1) of the human ear, has a proximal end 222, a body 226 and a distal end 230. In one embodiment of the present disclosure, proximal end 222 may have a circular opening leading to a cylindrical cavity within body 226. The circular opening of proximal end 222 is designed to fit conventional otoscope speculum 350 connected to an otoscope equipped with a light source and insufflation port for pneumatic otoscopy. Pressure-controlled air from the otoscope travels through speculum 350 to push cup-like cradle 340 forward toward tympanic membrane 22. Distal end 230 of drug delivery device applicator 300 may have a dome-shaped end 232 to facilitate drug delivery device applicator 300 penetration into and insertion along external auditory canal 20. The dome-shaped end 232 is hollow and may be composed of two or more leaflets 234 designed to mechanically open, upon pushing cup-like cradle 340, to form a distal circular opening. Cup-like cradle part 340 may be made of lateral wall 252 and circumferential wall 256, and designed to accommodate drug delivery device 10. In one embodiment of the present disclosure lateral wall 252 and circumferential wall 256 are joined by mechanism 250 that allows their separation when circumferential wall 256 encounters resistance during travel of Cup-like cradle part 340 along cylindrical cavity of body 226. One or more protuberances 254, which may be located proximate or as part of base of leaflets 234 may serve (a) to open the dome 232 at distal end 230 and (b) to block further advancement of circumferential wall 256 of the cup-like cradle thus causing lateral wall 252 to disengage from circumferential wall 256 and move along the opened dome while pushing forward drug delivery device 10 toward tympanic membrane 22.

Note that with the example provided above, as well as numerous other examples provided herein, interaction may be described in terms of two, three, or four elements. However, this has been done for purposes of clarity and example only. It should be appreciated that drug delivery device 10 (and its teachings) are readily scalable and can accommodate a large number of components, as well as more complicated/sophisticated arrangements and configurations. Accordingly, the examples provided should not limit the scope or inhibit the broad teachings of drug delivery device 10 as potentially applied to a myriad of other architectures.

Although the present disclosure has been described in detail with reference to particular arrangements and configurations, these example configurations and arrangements may be changed, and the features therefrom combined in different arrangements, without departing from the scope of the present disclosure. Moreover, the present disclosure is equally applicable to various technologies, aside from those disclosed herein, as these have only been offered for purposes of discussion.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

The invention claimed is:

1. An apparatus for insertion in an ear having an external auditory canal and a tympanic membrane, to treat middle ear infection, the apparatus comprising:
a drug delivery device for insertion into an external auditory canal, the drug delivery device having a cylindrically shaped shell having an overall flattened shape such that the height of the device is smaller than its diameter and having a lateral surface, an outer circumferential surface, an inner circumferential surface, and having a single cavity formed and bounded by said lateral surface and inner circumferential surface, wherein said cavity opens medially, and wherein the drug delivery device is preloaded with:
one or more pharmaceutically active agents;
one or more optional pharmaceutical additives and excipients; and
one or more optional other active ingredients;
wherein the at least one of the one or more pharmaceutically active agents, additives, excipients, and other active ingredients are contained within the cavity, wherein the lateral surface and outer circumferential surface of the drug delivery device are at least partially impermeable to at least one of the one or more pharmaceutically active agents, the one or more optional pharmaceutical additives and excipients, if present, and the one or more optional other active ingredients, if present, either alone or in combination, thereby allowing for selective directional and continuous release of the pharmaceutically active agents, the one or more optional pharmaceutical additives and excipients, if present, and the one or more optional other active ingredients, if present, either alone or in combination, onto the tympanic membrane through which the one or more pharmaceutically active agents enter the middle ear via diffusion;
wherein the one or more pharmaceutically active agents, the one or more optional pharmaceutical additives and excipients, if present, and the one or more optional other active ingredients, if present, are formulated in a form selected from the group consisting of a highly viscous solution, suspension, gel, paste, ointment, wax, cream, pressed powder, and tablet;
and wherein the apparatus is retained entirely within the external auditory canal proximate to the tympanic membrane.

2. The apparatus of claim 1, wherein the drug delivery device conforms to the profile of the external auditory canal.

3. The apparatus of claim 1, wherein the drug delivery device comprises a polymeric matrix structure.

4. The apparatus of claim 1, wherein the drug delivery device is annular in shape.

5. The apparatus of claim 1, further comprising:
one or more elements for handling the drug delivery device during insertion and removal of the drug delivery device into and out of the ear; wherein said one or more elements are part of the drug delivery device.

6. The apparatus of claim 1, further comprising:
one or more elements for positioning the drug delivery device within a drug delivery device applicator; wherein said one or more elements are part of the drug delivery device.

7. The apparatus of claim 1, further comprising:
a circumferential rim for temporarily immobilizing the drug delivery device proximate to the tympanic membrane.

8. The apparatus of claim 1, wherein the drug delivery device is made of one or more polymers selected from the group: natural polymers; synthetic polymers; swellable polymers; non-swellable polymers; stimuli-responsive polymers; erodible polymers; and non-erodible polymers.

9. The apparatus of claim 1, wherein the one or more pharmaceutically active agents are selected from one or more of the group: anti-bacterial agents; anti-viral agents; anti-fungal agents; disinfectant agents; analgesics; anti-inflammatory agents; immuno-suppressive agents; cerumenolytic agents; vestibular agents; and premedication agents.

10. The apparatus of claim 1, wherein the one or more optional pharmaceutical additives and excipients, if present, are selected from the group consisting of: dissolution agents; emulsifying agents; chelating agents; preservatives; cerumenolytic agents; and penetration enhancers.

11. The apparatus of claim 1, wherein the one or more pharmaceutically active agents, the one or more optional pharmaceutical additives and excipients, if present, and the one or more optional other active ingredients, if present, are incorporated into the drug delivery device.

12. The apparatus of claim 1, wherein the one or more pharmaceutically active agents, the one or more optional pharmaceutical additives and excipients, if present, and the one or more optional other active ingredients, if present, are carried by the drug delivery device for selective delivery through the tympanic membrane.

* * * * *